(12) United States Patent
Lang et al.

(10) Patent No.: US 6,796,353 B2
(45) Date of Patent: Sep. 28, 2004

(54) APPARATUS FOR HANDLING COVERSLIPS FOR SPECIMEN SLIDES

(75) Inventors: Anton Lang, Vienna (AT); Paul Wurzinger, Deutsch-Wagram (AT)

(73) Assignee: Leica Mikrosysteme GmbH, Vienna (AT)

( * ) Notice: Subject to any disclaimer, the term of this patent is extended or adjusted under 35 U.S.C. 154(b) by 7 days.

(21) Appl. No.: 10/225,625

(22) Filed: Aug. 22, 2002

(65) Prior Publication Data

US 2003/0047863 A1 Mar. 13, 2003

(30) Foreign Application Priority Data

Sep. 7, 2001 (DE) .......................................... 101 44 048

(51) Int. Cl.[7] .............................................. B65H 29/24

(52) U.S. Cl. ...................... 156/556; 156/571; 156/573; 156/108; 271/103; 221/211; 414/627

(58) Field of Search .......................... 156/99, 108, 295, 156/538, 539, 556, 569–573, 285, DIG. 30, DIG. 31, DIG. 37, DIG. 28, DIG. 42; 271/103, 106, 91, 95, 98, 102; 221/210–211; 414/627, 737

(56) References Cited

U.S. PATENT DOCUMENTS

| 3,826,485 | A | * | 7/1974 | Shindo ........................ 271/106 |
|---|---|---|---|---|
| 5,048,811 | A | * | 9/1991 | Hochbein ........................ 271/5 |
| 5,205,160 | A | * | 4/1993 | Gandini ........................ 73/113 |
| 5,542,658 | A | * | 8/1996 | Wirz et al. .................... 271/107 |
| 6,345,818 | B1 | * | 2/2002 | Stephan et al. ................ 271/91 |
| 6,382,693 | B1 | * | 5/2002 | Ljungmann ................ 294/64.1 |
| 6,652,217 | B2 | * | 11/2003 | Dettman et al. ............ 414/797 |

FOREIGN PATENT DOCUMENTS

| WO | WO 95/20176 | 7/1995 | |
|---|---|---|---|
| WO | WO 97/00461 | 1/1997 | |
| WO | WO 00/37986 | * 6/2000 | ........... G02B/21/34 |

* cited by examiner

*Primary Examiner*—Jeff H. Aftergut
*Assistant Examiner*—Jessica Rossi
(74) *Attorney, Agent, or Firm*—Hodgson Russ LLP

(57) ABSTRACT

An apparatus (1) for handling coverslips (20) for specimen slides (9) comprises a transport arm (8), a base block (3) mounted on the transport arm and having a having a notional center axis (3a), and at least two suction devices (4 and 5) carried by the base block (3), each suction device (4 and 5) having an end (4a and 5a) that comes into contact with a coverslip (2) and points away from the notional center axis (3a) of said base block (3). The base block (3) both removes a single coverslip (2) from a magazine (24), and deposits the removed coverslip (2) onto a specimen slide (9).

9 Claims, 4 Drawing Sheets

APPARATUS FOR HANDLING COVERSLIPS FOR SPECIMEN SLIDES

CROSS REFERENCE TO RELATED APPLICATIONS

This application claims priority of the German patent application 101 44 048.0 filed Sep. 7, 2001 which is incorporated by reference herein.

FIELD OF THE INVENTION

The invention concerns an apparatus for handling coverslips for specimen slides, the apparatus comprising a base block, a transport arm on which the base block is mounted, and at least two pickup means provided in the base block, each pickup means having an end that comes into contact with the coverslip, and each of the ends pointing away from the notional center axis of the base block.

The invention furthermore concerns a method for removing coverslips and placing them onto a specimen slide, the coverslips being deposited in a magazine.

BACKGROUND OF THE INVENTION

An automatic cover slipper is used to automatically position coverslips on a microscopy specimen slide and to cover a preparation present on the specimen slide. Coverslips of a wide variety of sizes are available in packages, usually of 100 units. Before the coverslipping operation, a single coverslip must be removed from a stack. This step is very critical, since the coverslips can adhere to one another because of their thinness (approx. 0.17 mm thick) and smooth surface. A further problem is glass breakage. The stack of coverslips sometimes contains broken coverslips, but manipulation in the coverslipper can also result in glass breakage. The existing art described below is not capable of proposing any solution to this problem.

Patent application WO 97/00461 discloses an apparatus for picking up and depositing coverslips. The pickup head comprises two suction cups pointing downward and outward at an angle. The coverslip assumes a concavely curved shape when it is being held by the suction cup. Provided between the suction cups is a piston that is preloaded by a spring and can be brought by a magnet coil into a position such that the piston does not touch the coverslip held by the suction cups. Once a coverslip has been picked up, if the piston is retracted by the magnet coil, a slight warping is exerted on the coverslip and detaches any further coverslips that may be adhering. A separate deposition head, which retains the coverslip with a suction cup and guides it over the specimen slide, is provided for deposition of the coverslip onto the specimen slide. The coverslip is pressed onto the specimen slide with a pivotably mounted lever and lastly deposited onto it. This apparatus for picking up and depositing coverslips disclosed here possesses a special configured head for each operation. This in turn increases the probability of damage to the coverslips being deposited.

WO 95/20176 discloses an instrument for automatic deposition of coverslips. The pickup head possesses suction cups, facing outward from the longitudinal axis of the pickup head, to which a vacuum can be applied individually. A piston that is mechanically preloaded downward with a spring is provided between the suction cups. In order to pick up a coverslip, the pickup head is pressed onto the coverslip stack until the suction cups are in contact with the topmost coverslip. The adhesion between the topmost coverslip and the coverslips below it is overcome by means of a shearing motion. As soon as the pickup head has completely grasped the coverslip, it transfers it to a deposition head that then deposits the coverslip onto the specimen slide. The high mechanical stress, the transfer of the coverslip from one station to a subsequent one, and the absence of automatic monitoring mean that this system cannot operate with sufficient confidence. It also definitely requires more frequent service as a result of its complexity.

An apparatus that both removes coverslips from a cover glass stack and deposits them onto a specimen slide is disclosed in U.S. Pat. No. 4,428,793. The apparatus comprises a pickup element and a first and second pushing element. The pickup element is configured as a suction cup, and the first and second pushing means engage at opposite ends of the coverslip. Upon removal of the coverslip from the coverslip stack, it is curved by the action of the first and second pushing elements, and thus detached from the coverslips adhering below. The high mechanical stresses as coverslips are picked up from the stack and deposited onto the specimen slide increase the probability of coverslip breakage, which negatively influences the efficiency of the apparatus.

SUMMARY OF THE INVENTION

It is the object of the invention to create an apparatus with which coverslips can be automatically removed from a coverslip stack and the risk of coverslip breakage is considerably reduced. A further intention is that deposition of the coverslips onto the specimen slide be accomplished as automatically as possible and without disruptions.

This object is achieved in that the base block provided on the transport arm in each case both removes a single coverslip from a magazine, and deposits the removed coverslip onto a specimen slide.

A further object of the invention is to create a method which makes possible reliable, accurate, and economical deposition of coverslips onto specimen slides.

This object is achieved by way of a method characterized by the following steps:

lowering a transport arm with a pivotable base block mounted thereon, at least two pickup means being provided in the base block, each pickup means comprising an end that comes into contact with the coverslip and each of the ends pointing away from the notional center axis of the base block;

picking up a coverslip with the ends of the pickup means, the coverslip resting against a continuously and uniformly curved surface of the base block; and lowering the transport arm onto the specimen slide, in which context the continuously and uniformly curved surface of the base block rolls onto the specimen slide and deposits the coverslip.

It is advantageous that with the apparatus, once the coverslip has been picked up from the magazine it need not be set down again or transferred to a further device for depositing the coverslips onto the specimen slide. This considerably reduces the risk of coverslip breakage. In addition, the apparatus works more effectively as a result. More specimen slides per unit time can be equipped with coverslips.

A further advantage is constituted by the fact that the base block of the apparatus comprises a continuously and uniformly curved surface beyond which the ends of the pickup means project. A defined contact of the coverslip is thereby achieved. In addition, contact in this form means that no points or edges are formed that would exert excessive pressure on the coverslip. A uniformly distributed force thus acts on the coverslip. Means for reducing the length of the pickup means are provided, so that as a result of the reduction in length, the coverslip is brought into contact with the continuously and uniformly curved surface. A particularly uniform distribution of force is obtained if the continuously and uniformly curved surface corresponds to the curved surface of a cylinder segment. In equally low-stress fashion, the base block is connected to the transport arm pivotably via an articulated joint.

In order to ensure automation of the apparatus, there is provided in the base block, between the at least two pickup means, a sensor which ascertains the presence and the condition of a coverslip that has been picked up. It is thereby possible to prevent broken coverslips from being deposited onto the specimen slide.

It is advantageous that the pickup means is configured as suction device; and that a suction cup is provided on each of the ends of the pickup means coming into contact with the coverslip.

In a particularly advantageous embodiment of the invention, the means for reducing the length of the pickup means is configured as a bellows. Upon application of a negative pressure, a coverslip that has been picked up is thus brought into contact with the continuously and uniformly curved surface of the base block.

Movability of the apparatus is ensured by the transport arm, which comprises a support element that is arranged substantially parallel to the surface of a specimen slide, an angled element movable linearly along the support element, and a lifting element movable along one limb of the angled element. The lifting element carries the base block at an end opposite the coverslips.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
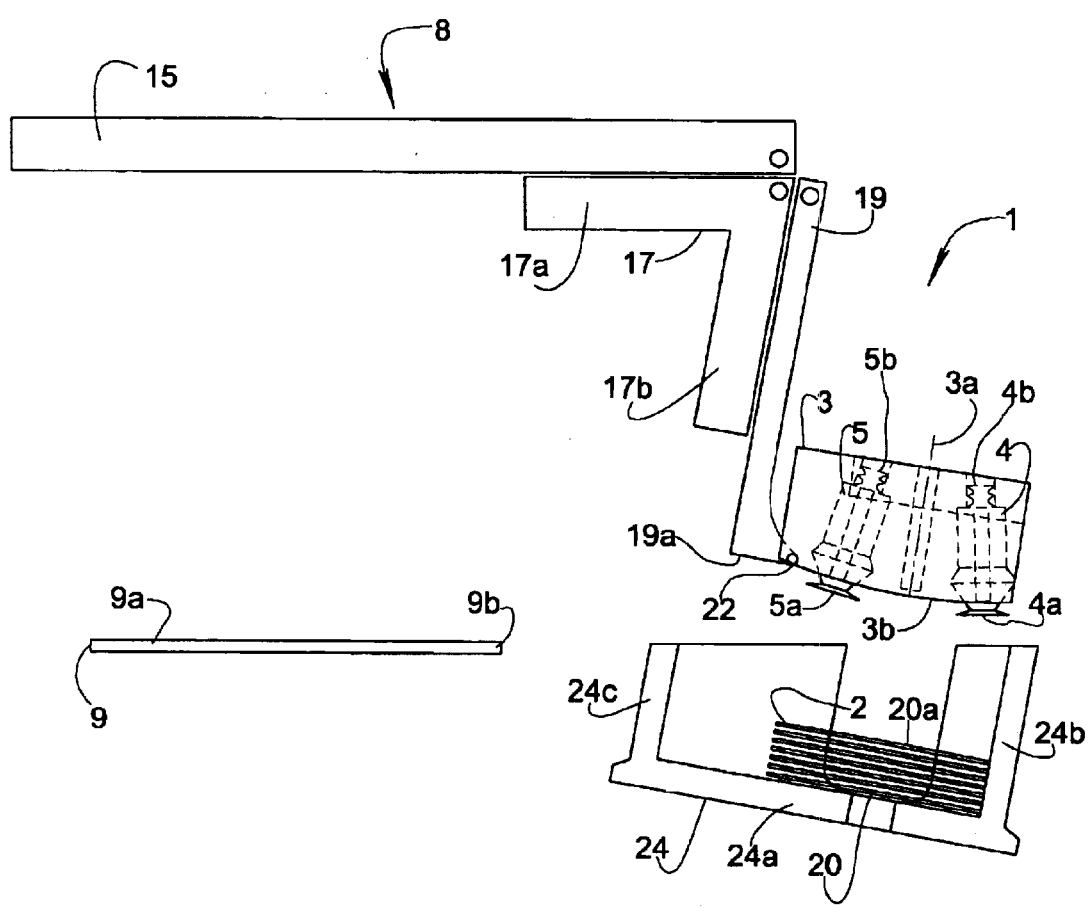
FIG. 1 schematically depicts the apparatus for handling coverslips, the coverslip that is to be removed having not yet been touched.

FIG. 1 schematically depicts apparatus 1 for handling coverslips 20, coverslip 2 that is to be removed having not yet been touched by apparatus 1. The apparatus comprises a base block 3 in which at least two pickup means 4, 5 are provided. In the embodiment depicted here, pickup means 4, 5 are embodied as suction devices. Each pickup means 4 and 5 possesses a respective end 4a, 5a that comes into contact with coverslip 2. Each of ends 4a and 5a is arranged in such a way that it points away from a notional center axis 3a of base block 3. Base block 3 itself is mounted on a transport arm 8. Transport arm 8 comprises a support element 15 that is arranged substantially parallel to surface 9a of a specimen slide 9. Provided on support element 15 is a linearly movable angled element 17 of which a first limb 17a is connected to support element 15 and a second limb 17b carries a lifting element 19 movable along said limb. Base block 3 is pivotably joined via an articulated joint 22 to lifting element 19 at an end 19a thereof located opposite coverslips 20. Base block 3 provided on transport arm 8 is configured in such a way that it both removes a single coverslip 2 from a magazine 24 and deposits onto a specimen slide 9 coverslip 2 that has been picked up. By means of lifting element 19, base block 3 is lowered into magazine 24 perpendicularly to surface 20a of coverslips 20. Magazine 24 is configured such that coverslips 20 are deposited in magazine 24 in the form of a stack, the magazine comprising a bottom 24a and sidewalls 24b and 24c mounted at right angles to bottom 24a; and magazine 24 is tilted from the horizontal so that one of sidewalls 24c forms a defined stop for coverslips 20 of the stack. This has the advantage that regardless of their length, coverslips 20 are each identically positioned with respect to an edge 9b of specimen slide 9 upon deposition onto specimen slide 9. For removal of a coverslip 2 from magazine 24, base block 3 is displaced into magazine 24 with lifting element 19. Base block 3 possesses a continuously and uniformly curved surface 3b beyond which ends 4a and 5a of the pickup means project. In a preferred embodiment, the continuously and uniformly curved surface corresponds to the curved surface of a cylinder segment. The two pickup means 4 and 5 each project with their ends beyond continuously and uniformly curved surface 3b. In this embodiment, ends 4a and 5a are configured as suction devices. A sensor 10 that ascertains the presence and condition of a coverslip 2 that has been picked up is provided in base block 3 between the at least two pickup means 4 and 5. In the preferred embodiment, sensor 10 is embodied as a capacitative sensor.

Figure 2:
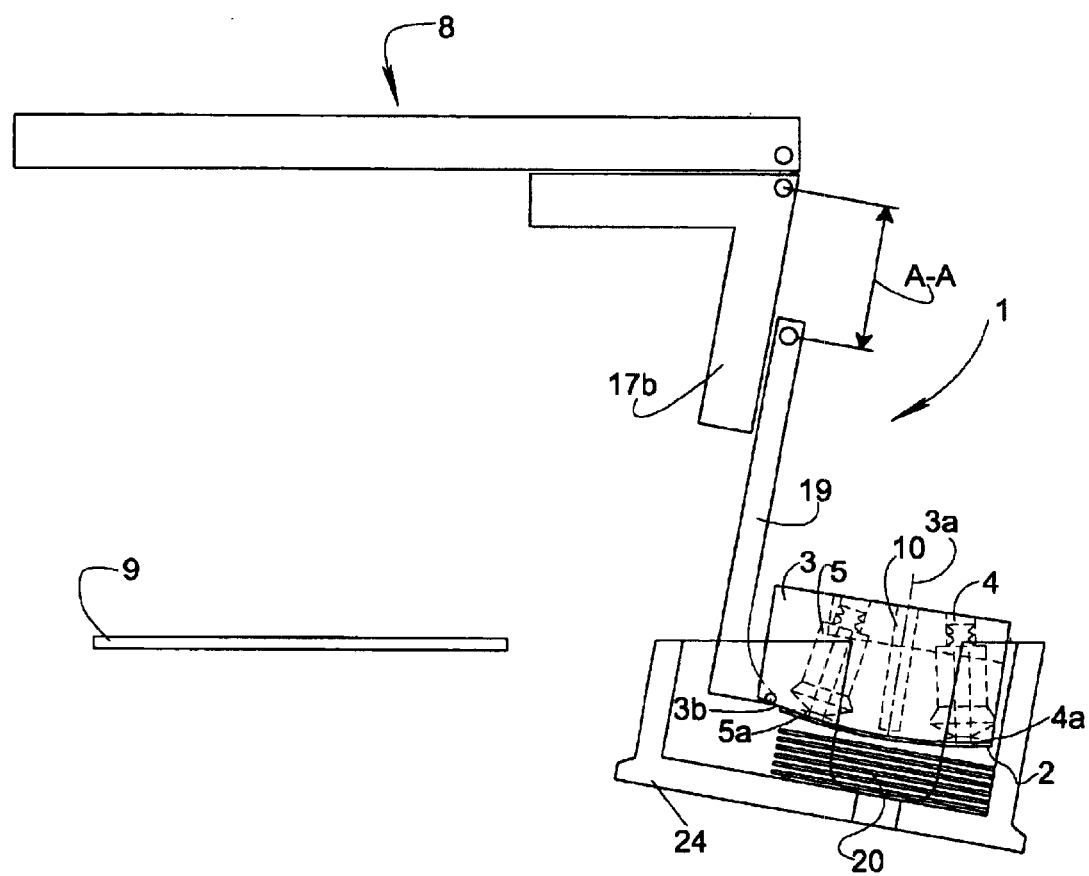
FIG. 2 schematically depicts the apparatus for handling coverslips, the coverslip that is to be removed having already been picked up in the magazine by the apparatus.

FIG. 2 schematically depicts apparatus 1 for handling coverslips 20, coverslip 2 in magazine 24 having already been removed by apparatus 1. Lifting element 19 that is movable along second limb 17b has been lowered into magazine 24 as indicated by arrow A—A. As a result, base block 3 and ends 4a and 5a of pickup means 4 and 5 projecting beyond base block come into contact with the topmost coverslip 2 present in magazine 24. A negative pressure is applied to pickup means 4 and 5 embodied as suction devices. Pickup means 4 and 5 are suction devices, and topmost coverslip 2 is grasped as a result of the negative pressure applied to suction devices 4 and 5. Suction devices 4 and 5 possess a bellows (means 4b and 5b for reducing the length of pickup means 4 and 5) that has contracted as a result of the negative pressure and thereby brings coverslip 2 into contact against curved surface 3b of base block 3. The curvature is selected so that further coverslips adhering to the topmost coverslip 2 fall back onto the stack of coverslips 20 in magazine 24. Lifting element 19 is then raised, together with base block 3 and coverslip 2 that has been picked up, in the direction of arrow A—A.

Figure 3:
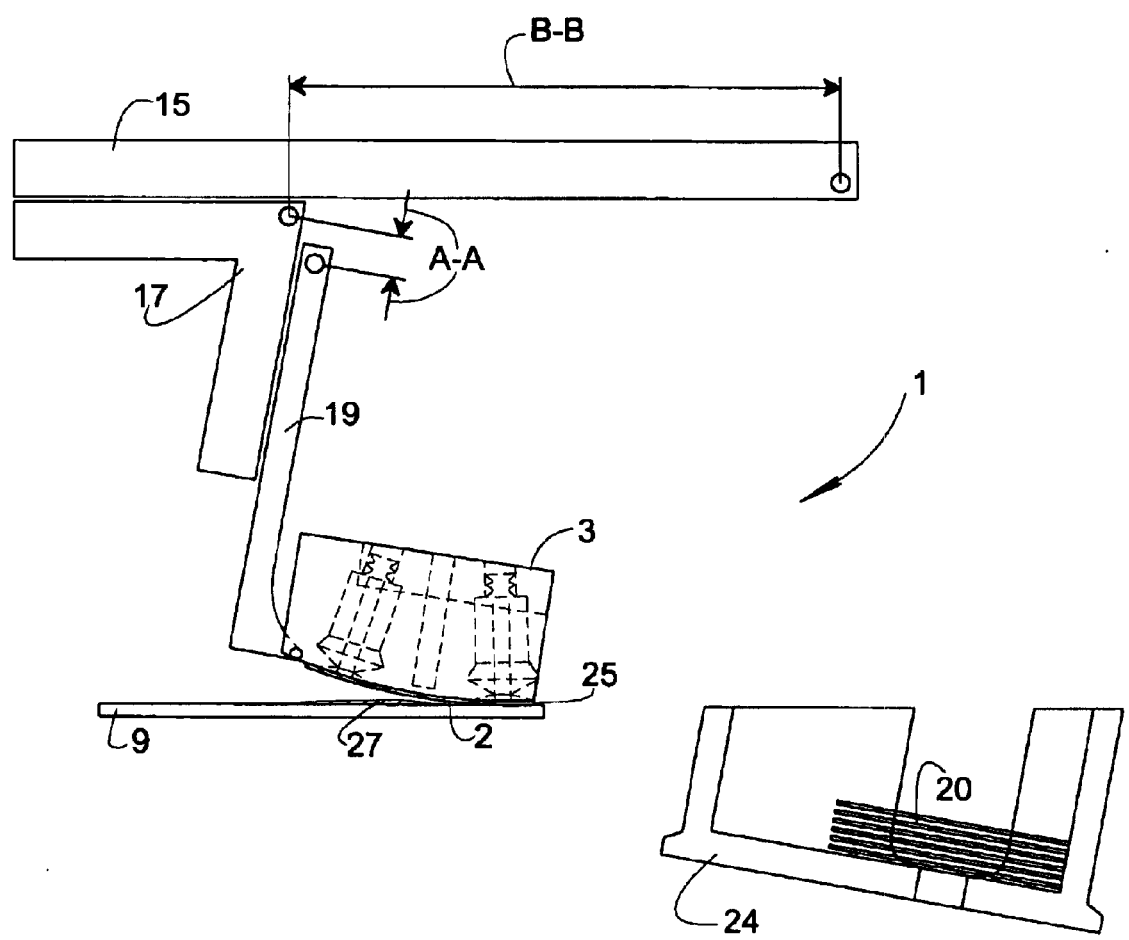
FIG. 3 schematically depicts the apparatus for handling coverslips, the coverslip having already been brought at one end into contact with the specimen slide.

FIG. 3 schematically depicts apparatus 1 for handling coverslips 20, coverslip 2 having already been brought at one end 25 into contact with specimen slide 9 by means of apparatus 1. After lifting element 19 has been raised out of magazine 24, it is displaced together with angled element 17, by way of support element 15, in the direction of arrow B—B. Base block 3 thus travels into a position above specimen slide 9. At this time, an adhesive 27 has already been applied onto specimen slide 9. By means of lifting element 19, base block 3 is lowered onto specimen slide 9. This occurs in the direction of arrow A—A. End 25 of coverslip 2 is the first to contact specimen slide 9. The application pressure of coverslip 2 on specimen slide 9 is adjusted using suitable means (e.g. springs or weights) that are not depicted. This is necessary in particular for uniform distribution of adhesive 27.

Figure 4:
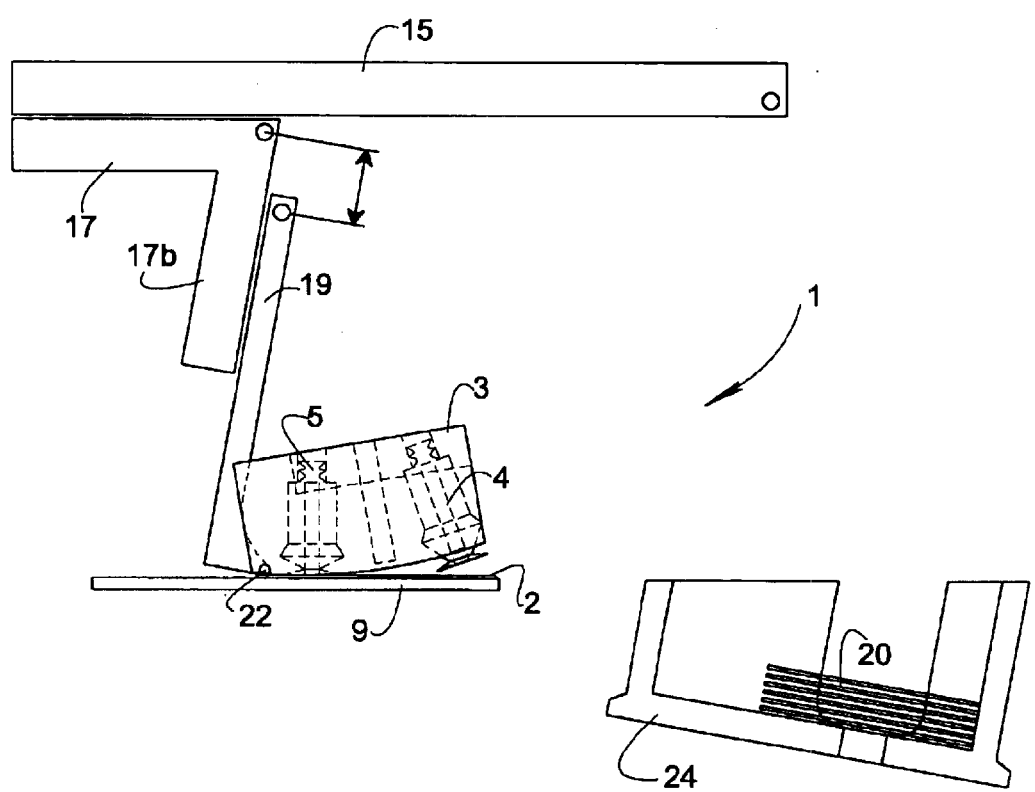
FIG. 4 schematically depicts the apparatus for handling coverslips, the coverslip having already been completely deposited onto the specimen slide by the apparatus

FIG. 4 schematically depicts apparatus 1 for handling coverslips 20, coverslip 2 having already been completely deposited onto specimen slide 9 by apparatus 1. A rolling motion of base block 3 results in complete deposition of coverslip 2 onto specimen slide 9. Base block 3 is joined to lifting element 19 via an articulated joint 22. Base block 3 is pivoted about articulated joint 22 and in the process rolls along surface 9a of specimen slide 9. Articulated joint 22 is selected in such a way that in order to achieve an almost exclusive rolling motion with no lateral shifting, angled element 17 remains stationary along support element 15. The rolling motion of base block 3 is accomplished solely by way of the lowering of lifting element 19 along second limb 17b of angled element 17. The rolling motion of base block 3 can be controlled both via a lowering of lifting element 19 and via an independent rotation mechanism (e.g. motor) about articulated joint 22. Coverslip 2 is now completely resting on specimen slide 9. The negative pressure at first suction device 4 was shut off at the beginning of the rolling motion. Before base block 3 is raised, the negative pressure at second suction device 5 is switched off. Base block 3 is raised, and is ready to pick up a further coverslip 2 from magazine 24.

The invention has been described with reference to a particular exemplary embodiment. It is nevertheless self-evident that changes and modifications can be made without thereby leaving the range of protection of the claims below.

PARTS LIST

| | |
|---|---|
| 1 | Apparatus |
| 2 | Coverslip |
| 3 | Base block |
| 3a | Center axis |
| 3b | Continuously and uniformly curved surface |
| 4 | Pickup means |
| 4a | End of pickup means |
| 4b | Means for reducing length |
| 5 | Pickup means |
| 5a | End of pickup means |
| 5b | Means for reducing length |
| 8 | Transport arm |
| 9 | Specimen slide |
| 9a | Surface of specimen slide |
| 9b | Edge of specimen slide |
| 10 | Sensor |
| 15 | Support element |
| 17 | Angled element |
| 17a | First limb |
| 17b | Second limb |
| 19 | Lifting element |
| 19a | End of lifting element |
| 20 | Coverslips |
| 20a | Surface of coverslips |
| 22 | Articulated joint |
| 24 | Magazine |
| 24a | Bottom |
| 24b | Sidewall |
| 24c | Sidewall |
| 25 | End of coverslip |
| 27 | Adhesive |
| A-A | Arrow |
| B-B | Arrow |

What is claimed is:

1. An apparatus (1) for handling coverslips (20) for specimen slides (9), said apparatus (1) comprising:
   a transport arm (8);
   a base block (3) mounted on said transport arm, said base block (3) having a notional center axis (3a) and a continuously and uniformly curved surface (3b);
   an articulated joint (22) pivotably connecting said base block to said transport arm;
   at least two pickup means (4 and 5) carried by said base block (3), each pickup means (4 and 5) having an end (4a and 5a) that comes into contact with a coverslip (2), and each of said ends pointing away from said notional center axis (3a) of said base block (3) and projecting beyond said curved surface (3b); and
   means (4b and 5b) for reducing the length of said pickup means (4 and 5);
   wherein said base block (3) mounted on said transport arm (8) both removes a single coverslip (2) from a magazine (24), and deposits said removed coverslip (2) onto a specimen slide (9).

2. The apparatus as defined in claim 1, wherein said continuously and uniformly curved surface (3b) corresponds to a curved surface of a cylinder segment.

3. The apparatus as defined in claim 1, wherein said pickup means (4 and 5) are configured as suction devices; and a suction cup is provided on each of said ends (4a and 5a) of said pickup means coming into contact with said coverslip (2).

4. The apparatus as defined in claim 1, wherein said means for reducing the length of said pickup means (4 and 5) is configured as a bellows, and a coverslip (2) that has been picked up is thus brought into contact with said continuously and uniformly curved surface (3b) of said base block (3).

5. The apparatus as defined in claim 1, further comprising a magazine wherein said coverslips (20) are deposited in said magazine (24) in the form of a stack, said magazine comprising a bottom (24a) and sidewalls (24b and 24c) mounted at right angles to said bottom; and said magazine (24) being tilted from the horizontal so that one of said sidewalls forms a defined stop for coverslips (20) of said stack.

6. The apparatus as defined in claim 1, wherein there is provided in said base block (3), between said at least two pickup means (4 and 5), a sensor (10) which ascertains the presence and the condition of a coverslip (2) that has been picked up.

7. The apparatus as defined in claim 6, wherein said sensor (10) is a capacitative sensor.

8. An apparatus (1) for handling coverslips (20) for specimen slides (9), said apparatus (1) comprising:
   a transport arm (8);
   a base block (3) mounted on said transport arm, said base block (3) having a notional center axis (3a); and
   at least two pickup means (4 and 5) carried by said base block (3), each pickup means (4 and 5) having an end (4a and 5a) that comes into contact with a coverslip (2), and each of said ends pointing away from said notional center axis (3a) of said base block (3);
   wherein said transport arm (8) comprises a support element (15) that is arranged substantially parallel to a surface (9a) of a specimen slide (9); an angled element (17) movable linearly along said support element (15) and having a first limb (17a) and a second limb (17b); and a lifting element (19), movable along said second limb (17b) of said angled element (17), said lifting element carrying said base block (3) at an end (19a) thereof opposite said coverslips; and
   wherein said base block (3) mounted on said transport arm (8) both removes a single coverslip (2) from a magazine (24), and deposits said removed coverslip (2) onto a specimen slide (9).

9. The apparatus as defined in claim 8, wherein said end (19a) of said lifting element (19) opposite said coverslips is joined to said base block (3) via an articulated joint (22).

* * * * *